United States Patent
Schmid et al.

(10) Patent No.: US 6,911,441 B2
(45) Date of Patent: Jun. 28, 2005

(54) PROLONGED RELEASE PHARMACEUTICAL COMPOSITION

(75) Inventors: Peter Schmid, Waldbrunn (DE); Alexander Boettner, Frankfurt (DE); Carsten Schmidt, Mainz (DE); Mark Allan, Hofheim (DE); Carole Barbot, Boos (FR)

(73) Assignee: Akzo Nobel N.V., Arnhem (NL)

( * ) Notice: Subject to any disclaimer, the term of this patent is extended or adjusted under 35 U.S.C. 154(b) by 148 days.

(21) Appl. No.: 10/320,250

(22) Filed: Dec. 16, 2002

(65) Prior Publication Data

US 2004/0115260 A1 Jun. 17, 2004

(51) Int. Cl.[7] .............................................. A61K 31/546
(52) U.S. Cl. ....................................... 514/202; 514/207
(58) Field of Search ................................. 514/202, 203, 514/204, 206, 207

(56) References Cited

U.S. PATENT DOCUMENTS

| | | | |
|---|---|---|---|
| 3,920,819 A | 11/1975 | Stephens et al. | |
| 4,258,041 A | * 3/1981 | O'Callaghan et al. | ...... 514/203 |
| 4,341,777 A | 7/1982 | White | |
| 5,013,833 A | * 5/1991 | Crisp et al. | .................. 540/222 |

FOREIGN PATENT DOCUMENTS

| | | |
|---|---|---|
| GB | 792545 | 7/1956 |
| GB | 2 087 236 A | 11/1981 |
| WO | WO 87/03876 | 7/1987 |
| WO | WO 00/61149 | 10/2000 |
| WO | WO 03/063877 A1 | 8/2003 |

OTHER PUBLICATIONS

XP-002240092, JP 19850075377, 1985.

* cited by examiner

*Primary Examiner*—Barbara P. Badio
(74) *Attorney, Agent, or Firm*—William M. Blackstone (57) ABSTRACT

Novel pharmaceutical compositions of a cephalosporin in a prolonged release vehicle, comprising an oil and aluminium distearate, provide a prolonged duration of effective blood-plasma concentration of the cephalosporin after injection to animals.

12 Claims, 12 Drawing Sheets

Figure 1: Cefquinome plasma concentrations in cattle after SC administration of Cefquinome Sulphate formulations at a dose rate of 5.0 mg/kg bw (log-linear curve, mean values (n=3))

Figure 2: Cefquinome plasma concentrations [μg/mL] in dog after SC administration of Cefquinome Sulphate 7.5% V 078 SL5 16-18 at a dose rate of 10 mg/kg bw (log-linear curves for individual animals)

Figure 3: Cefquinome plasma concentrations [μg/mL] in pig after IM administration of Cefquinome Sulphate 7.5% V 078 SL5 16-18 at a dose rate of 10 mg/kg bw (log-linear curves for individual animals)

Figure 4: Cefquinome plasma concentrations [μg/mL] in cattle after SC administration of Lot No.: 960906 (log-linear curves for individual animals)

Figure 5: Cefquinome plasma concentrations [μg/mL] in cattle after SC administration of Lot No.: 960907 (log-linear curves for individual animals)

Figure 6: Cefquinome plasma concentrations [μg/mL] in cattle after SC administration of Cobactan® 2.5 % and Lot 970802, 970803, 970804, 970805, 970903 at a dose rate of 5 mg/kg bw (log-linear curves, mean values*)

*Individual values below the limit of quantification were assumed to be equal to 0.0 μg/L for the purpose of calculating the means Figure 7: Cefquinome plasma concentrations [µg/mL] in cattle after SC administration of preparations a-e at a dose rate of 5 mg/kg bw (preparation a-d: n=10, preparation e, n=3) (log-linear curves, mean values)

Figure 8: Cefquinome plasma concentrations [µg/mL] in cattle after SC administration of *Cefquinome LA* in a dose rate of 5 mg/kg bw (log-linear curves, mean values*)

*Individual values below the limit of quantification were assumed to be equal to 0.0 µg/L for the purpose of calculating the means Figure 9: Cefquinome concentrations in bovine plasma after a single intramuscular injection of cefquinome -p-hydroxybenzoate in miglyol 812 at a dosage of 5mg Cefquinome /kg bw (individual animals)

Figure 10: Cefquinome plasma concentrations [μg/mL] after IM administration of formulation 01, 02 and 03 to cattle at a dose rate of of 3 mg/kg bw / 5 mg/ kg bw ( log-linear curve, mean values (n=3)

Figure 11: Cefquinome plasma concentrations [μg/mL] after SC administration of formulation 01, 02 and 03 to cattle at a dose rate of of 3 mg/kg bw / 5 mg/ kg bw ( log-linear curve, mean values (n=3)

Figure 12: Cefquinome plasma concentrations [μg/mL] after IM administration of formulation 01, 02 and 03 to pigs at a dose rate of of 6 mg/kg bw / 10 mg/ kg bw ( log-linear curve, mean values (n=3)

PROLONGED RELEASE PHARMACEUTICAL COMPOSITION

The present invention is concerned with a pharmaceutical composition comprising a cephalosporin and a prolonged release vehicle, a process for preparing said composition and its use for the treatment of infectious diseases in animals.

In the prior art many different concepts of prolonged release of pharmaceutical compositions for parenteral use in humans and animals have been described, e.g. use of low water soluble forms or complexes of active ingredients, use of liposomes, microspheres and lipospheres formulations, polymer formulations, oil based formulations, gel formulations etc. Some of them have been proposed for the use with antibiotic compounds.

The U.S. Pat. No. 4,029,782 discloses an aqueous suspension of cefazolin in a prolonged release vehicle composed of water, lecithin, a pharmaceutically acceptable surfactant and a viscosity modifier. Cefazolin is a first generation cephalosporin that is active on gram positive cocci, including *staphylococcus* spp. and *streptococcus* spp. but has only moderate activity against a limited number of aerobic gram negative bacilli, including *E. coli, Klebsiella pneumoniae* (Jones R N et al, J Antibiot 30, 576–582, 1977).

The UK patent application GB 2,232,082 discloses a prolonged release system that is based on oil (Miglyol® 840)/thickening agent (aluminiumstearate) in a composition together with monodicaprylate to promote an initial quick release of amoxicillin. WO 94/21267 provides a prolonged release tylosin preparation in Neobee oil/ aluminiumtristearate. European patent application EP 872, 232 describes a prolonged release system for tylosin comprising aluminiumstearate, a buffer and an emulsifying agent.

EP 356,325 discloses a prolonged release system for tetracycline antibiotics that comprises a glyceride (Miglyol®) together with a cellulose polymer.

French patent application FR 2685203 discloses a prolonged release system for amoxicillin in Miglyol®/cellulose based excipients composition.

However, the described prolonged release compositions, that are based on oil and a thickening agent have been not applied for the cephalosporin class of antibiotics, especially for modern cephalosporins of the third or fourth generation with a broad spectrum against important pathogens.

The administration of antibiotics to animals, especially to livestock, such as cattle and pigs, is a very labour intensive work and causes stress and loss of body weight to the animals. On the other hand the frequent administration of a highly active antibacterial compound as a modern cephalosporin to companion animals, such as e.g. dogs and cats requires frequent visits to the veterinarian which is inconvenient to the owner and stressful for the companion animal.

An advantageous pharmaceutical composition for the cephalosporin for veterinary application would be one, that enables a single injection, to provide efficacious concentration levels of the active compound in blood plasma of the treated animals over a prolonged period preferably over a 32 hours period. Besides the duration of release for such prolonged release compositions the technical features of the pharmaceutical formulation, e.g. easiness of application (syringeability and re-suspendability), side effects (local tolerance) and residues in the animal body (especially in livestock) are important features.

Although such compositions for prolonged release of pharmaceuticals are already described in prior art, a prolonged release composition for a cephalosporin has not yet been allied in practice in the veterinary market.

It would therefore be desirable to have a technically feasible formulation with an acceptable level of side effects and residues available that allows the release of an effective amount of a cephalosporin antibiotic over a prolonged time.

An injectable suspension of cefquinome is available on the veterinary market (sold under the trademark Cobactan® by Intervet International b.v., Boxmeer, The Netherlands) containing 25 mg/ml of cefquinome sulphate. An intramuscular or subcutaneous injection of this product at a dose of 1 mg/kg bodyweight cefquinome sulphate results in an efficacious plasma concentration over a period of 8–12 hours. A treatment with daily injections for 3–5 consecutive days is therefore recommended.

It would therefore be desirable to have a technically feasible formulation with an acceptable level of side effects and residues available that allows the release of an effective amount of cefquinome over a prolonged time. This would allow the use of this modem compound under conditions were a repeated administration of a compound is not desirable.

Several attempts have been taken by the inventors to develop such a prolonged release composition of such a modern cephalosporin compound, that were based on the information available from the prior art, but none of these proposed formulations fulfilled the needs of an appropriate prolonged release composition as described above.

These attempts include the use of a cephalosporin-based formulation with:
1) oily excipients only (ethyloleate: example 6, 7, 8, 9/Miglyol®: example 9)
2) thickening agents (alone or in combination with oil) other than aluminiumdistearate according to the current invention
   cellulose based excipients (example 5, 6 and 8),
   starch glycollate sodium based excipients (example 8),
3) microencapsulation/microspheres (example 7)
4) SABER® delivery system (example 10)

Details of the obtained results with the different formulations are summarised in FIGS. 4 to 12.

The duration of the efficacious plasma level for most of the formulations did not show an appropriate prolonged release profile. In case of one cellulose-based formulation of example 6 and the microspheres formulation in example 7 the technological features of the formulation were not suitable for a pharmaceutical product. In both cases the re-suspendability of the formulation was impossible. One of the SABER® formulations in example 10 provided a prolonged release profile of cefquinome. The reason for not considering this formulation further was the fact, that residues of the carrier were still detectable in the animal body during investigations 6 months after administration. This is not acceptable for a pharmaceutical formulation, especially if this formulation will be used in meat producing animals (livestock).

Thus, a need exists for a pharmaceutical composition for prolonged release for cephalosporins that overcome one or more of the limitations of the prior art. Such a composition provides a prolonged release formulation for cephalosporins that has acceptable technical features and allows the use of cephalosporin antibiotics under conditions were the repeated application of the compound would not be desirable.

The present invention provides a composition for cephalosporins with such advantageous properties.

SUMMARY OF THE INVENTION

The present invention provides a pharmaceutical composition comprising a cephalosporin and a prolonged release vehicle characterised in that the prolonged release vehicle comprises a mixture of an oil and aluminium distearate.

A prolonged release vehicle is a composition that releases the cephalosporin in a form which results in a prolonged effect, in particular prolonged duration of effective blood plasma concentration of the cephalosporin, compared to the pharmaceutical acceptable oil alone.

The composition according to the invention comprises an aluminiumdistearate as a thickening agent or alternatively mixtures of the aluminiumdistearate with other thickening agents known in the art for parenteral pharmaceutical use.

An aluminiumstearate is a compound of aluminium with a mixture of solid organic acids obtained from fats and consisting chiefly of variable proportions of aluminiumstearate and aluminiumpalmitate. Typically aluminiumstearate comprises organic solid acids obtained from fats of C14 to C26 fatty acids.

Aluminium monostearate (USP-NF19) is a compound of aluminium with a mixture of solid organic acids obtained from fats and consisting chiefly of variable proportions of aluminiummonostearate and aluminium-monopalmitate. It contains the equivalent of not less than 14.5 percent and not more than 16.5% of $Al_2O_3$, (equivalent to an aluminium content of 7.7% to 8.7% by weight) calculated on the dried basis.

The type of aluminium stearate to be used in the present invention, hereafter referred to as aluminium distearate comprises the equivalent of less than 7.5% by weight of aluminium, calculated on the dried basis. The aluminium content was measured by Atom Absorption Spectroscopy (AAS).

Preferred is aluminium distearate that comprises the equivalent of 3.0 to 7.0% by weight of aluminium, even more preferred with an aluminium content of 4.0 to 6.0% and especially preferred 4.5 to 5.0% by weight (measured by AAS).

Especially useful is the compound described in CAS 97404-28-9, such as e.g. "Aluminiumstearate M 132H6" of Stockbridge Ltd.

A thickening agent in an injectable pharmaceutical formulation in general is useful to provide good suspending properties and increases the viscosity of the composition without negatively affecting the syringeability.

By syringeable it is meant that the suspension can be withdrawn easily from an ampoule/vial into a syringe with a 16 to 18 gauge needle and subsequently injected from such a syringe through the 16 to 18 gauge needle intramuscularly (im) or subcutaneously (sc).

In a preferred embodiment a composition according to the invention is provided, characterised in that it comprises aluminium distearate in an amount of 1.0 to 4.0% by weight, preferred 2.5 to 3.5% by weight, most preferred 3.0% by weight.

By "by weight" in this patent application it is meant a percentage by weight of the total composition.

The prolonged release vehicle further comprises a pharmaceutical acceptable oil. Oils that can be used in pharmaceutical compositions are in general natural, e.g. vegetable, semi-synthetic or synthetic mono-, di- or tri glyceride. Vegetable oils are e.g. sesame oil, olive oil, cottonseed oil, castor oil, arachis oil, coconut oil.

In a preferred embodiment the pharmaceutical composition according to the invention is characterised in that the oil is a low viscosity medium chain triglyceride or a mixture of medium chain triglycerides.

Medium chain triglycerides (MCT) have fatty acid chains of 6–12 carbon atoms and for the medically refined grades of MCT oil each chain has 8–10 carbon atoms.

The MCT oil may comprise either triglycerides of the C8–C10 fatty acids, or propylene glycoldiesters of these fatty acids or a mixture of both triglycerides and propylene glycol diesters. Preferably these C8–C10 fatty acids are fully saturated, such as n-caprylic and n-capric acids. These are conveniently prepared by the commercial fractionating of naturally occurring vegetable (e.g. coconut) oil to give mainly C8–10 fatty acids followed by esterification of these acids with a chosen alcohol.

Fractionated vegetable oil having the desired composition is commercially available. Proprietary examples of such oils are Miglyol® 812 as capric/caprylic triglycerides and Miglyol® 840 as propylene glycol dicaprylate/caprate.

Equivalents of these oils are for example: Aldo® MCT KFG, Aldo® TC, Calgene CC-33, Calgene CC-33-F, Calgene CC-33-L, Calgene CC-33-S, Captex® 300, Captex® 355, Crodamol GTCC, Estasan GT 8-40 3578, Estasan GT 8-60 3575, Estasan GT 8-60 3580, Estasan GT 8-65 3577, Estasan GT 8-65 3581, Estasan GT 8-70 3579, Labrafac® LIPO, Labrafac® lipophile WL 1349, Lexol® GT-855, Lexol® GT-865, Miglyol® 810, Miglyol® 812, Myritol® 312, Myritol® 318, Neobee® 1053, Neobee® M-5, Neobee® O, Pelemol® CCT, Standamul® 318, Standamul® 7105 and Calgene CC-22, Calgene CC-22-S, Captex® 200, Lexol® PG-865, Miglyol® 840, Myritol® PC, Neobee® 1054, Neobee® M-20, Pelemol® PDD, Standamul® 302.

Most preferred is Miglyol® grade 812.

Cephalosporins are semisynthetic antibiotics derived from cephalosporin C, a natural antibiotic produced by the mould *Cephalosporium acremonium*. Cephalosporins belong to the class of β-lactam antibiotics and are classified as first- (e.g. cephalothin, cephaloridine, cefazolin), second- (cefamandole, cefuroxime, cefoxitin), third- (e.g. cefotaxime, ceftriaxone, cefoperazone) or fourth-generation (cefepime, cefpirome, cefquinome) products according to the order of their introduction and the position and type of side-chain that has been incorporated into the basic molecule. At present cephalosporins are widely used for the treatment of infections.

Cefotaxime was the first representative of the modern third and fourth generation semi-synthetic aminothiazolyl cephalosporins, followed by a series of polar cephalosporins. From these compounds cefpirome was selected for development in human medicine. Cefquinome is another representative of this group.

The term "cephalosporins" when used herein includes pharmaceutically acceptable salts and esters thereof.

Cefquinome (INN-International Nonproprietary Name) is the first fourth-generation cephalosporin developed for use in veterinary medicine. It is a semi-synthetic aminothiazolyl cephalosporin resembling cefotaxime, but with a bicyclic pyridinium group at the C-3 position (Isert et al, Seibert et al, 29$^{th}$ Interscience Conference on Antimicrobial Agents and Chemotherapy Houston, Tex., 1989).

The fourth generation cephalosporins possess favourable chemotherapeutic properties, i.e. a broad spectrum activity against a wide range of gram positive and gram negative organisms that are important in human and veterinary medicine and low rates of adverse effects (Limbert et al, Antimicrob Agents Chemotherap 35, 14–19, 1991, Caprille et al; J. Vet. Pharmacol. Ther. 11, 1–32, 1988)). Cefquinome is described to be stable against chromosomally and plasmid encoded lactamases.

Cefquinome has been found to be especially useful in treatment of respiratory infections in livestock (e.g. cattle and pigs (particularly *Mannheimia haemolytica* infection in cattle) when administered by injection. The MIC$_{90}$ for *Mannheimia haemolytica*, which is known to be one of the most common pathogens in respiratory tract infections in cattle is e.g. 0.25 µg/mL. The minimum plasma concentration level of an antibiotic is the level that is considered to be efficacious in the control of a pathogen and is determined by the MIC$_{90}$ (Minimum Inhibitory Concentration).

In a preferred embodiment the current invention provides a pharmaceutical composition characterised in that the cephalosporin is a cefquinome.

The term "cefquinome" when used herein includes pharmaceutically acceptable salts and esters thereof.

Various crystalline cephalosporin salts have been proposed for the treatment of bacterial infections, e.g. cefquinome dihydrochloride or cefquinome sulphate or crystalline cephalosporin addition salts with particularly low solubility e.g. cefquinome 6 hydroxynaphtoate (cefquinomenaphtoate) and cefquinome 2,4 dihydroxybenzoate (cefquinome hydroxybenzoate). In general all pharmaceutically acceptable cephalosporin salts can be incorporated in the current pharmaceutical composition. Good results were obtained with cefquinome sulphate.

Therefore in a preferred embodiment the current invention provides a pharmaceutical composition characterised in that the cefquinome is cefquinome sulphate.

A typical pharmaceutical composition according to the invention comprises 2.0 to 20.0% by weight of a cephalosporin as defined above. Preferably the pharmaceutical composition comprises 5.0 to 15.0%, most preferred 7.5 to 10.0% by weight of a cephalosporin.

The particle size of the active ingredient in the suspension can influence the re-suspendability and syringeability i.e. it should be small enough to prevent compaction or caking and to facilitate re-suspension. The cephalosporin utilised in the composition according to the current invention can be used in a micronised or non-micronised form. A desired reduction of particle size of the cephalosporin can be in general achieved by micronisation by an air jet mill, or by milling of the compound or wet milling of the suspension.

The pharmaceutical composition according to the current invention may further comprise additional pharmaceutical excipients known in the art. Such pharmaceutical excipients are e.g. described in "Gennaro, Remington: The Science and Practice of Pharmacy" (20. Edition, 2000), incorporated by reference herein.

Examples of such pharmaceutical excipients are carrier materials, such as starch, starch derivatives, waxes, natural or hardened oils; liquids such as glycerin or polyols; vegetable oils; polymers or copolymers such as copolymers from glycolic acid and lactic acid; surfactants; stabilizers; emulsifiers; disperging agents; thinners; thickening agents; preservation agents; buffer agents; salts and antioxidants.

The pharmaceutical composition contemplated herein can, if desired, include more than one pharmacologically active ingredient.

The current invention further provides a process for preparing an pharmaceutical composition according to the invention comprising the steps of mixing the oil and the aluminium distearate to create the prolonged release vehicle and suspending the cephalosporin in the prolonged release vehicle.

More specifically the current invention provides a process according to the invention characterised in that the aluminium distearate is added to the oil under gentle stirring and heating to form the prolonged release vehicle and the mixture is allowed to cool before adding the cephalosporin.

Even more specifically a process for preparing the prolonged release pharmaceutical composition is provided comprising in general the steps of preparing the prolonged release vehicle by mixing and homogenisation of the aluminium distearate with the oil and applying sufficient heat to permit adequate dissolution, allowing the mixture to cool and suspending the cephalosporin in the prolonged release vehicle which is subjected to high shear mixing to deposit the aluminium distearate.

A more detailed description of the manufacturing process is provided in example 1.

A more specific composition according to the present invention typically contains 7.5 to 10.0% of cefquinome sulphate, 2.5 to 3.5% of aluminium distearate and up to 100% of Miglyol® grade 812.

An even more specific composition according to the present invention typically contains 7.5% of cefquinome sulphate, 3.0% of aluminium distearate and up to 100% of Miglyol® grade 812.

Furthermore the current invention provides the use of a cephalosporin in a prolonged release vehicle comprising a mixture of an oil and aluminium distearate for the manufacture of a medicament for the treatment of infectious diseases in animals.

The composition according to the invention can be applied to an animal in general by all application forms known in the art. Generally the administration to the animal is done orally or parenterally. While the pharmaceutical composition according to the current invention is preferably administered parenterally, e.g. by intramuscular or subcutaneous injection, treatment via alternative routes is also possible.

In general the composition according to the current invention can be administered to all species of animals that need treatment or prevention of bacterial infections such as pigs, cattle, horses, goats, sheep, cats, dogs, poultry and fish.

Specific diseases that can be are bacterial infections of respiratory tract, uro-genital tract, soft tissue- and skin infections and mastitis, metritis.

The particular amount of prolonged release formulation required for a particular treatment will vary, depending upon the species, age and weight of the host animal being treated, the particular disease to be guarded against, or treated, as well as the specific antimicrobial agent selected for the treatment, the route and the frequency of administration.

For example the dose of cefquinome sulphate for the treatment of horses, sheep, goat, poultry and fish is between 5 to 10 mg/kg bodyweight. For cattle a dosage of 5 mg/kg bodyweight is recommended and for the application to pig, dog and cat a dosage of 10 mg/kg bodyweight.

EXAMPLES

Example 1

Preparation of a 7.5% Cefquinome Sulphate Composition (100 kg)

| | |
|---|---|
| 9.4 kg | cefquinome sulphate (containing 79.8% of cefquinome) |
| 3.0 kg | aluminium distearate M 123 H6 |
| up to 100 l | Miglyol® 812 |

1. Heat Miglyol® 812 until 130° C.
2. Disperse aluminiumstearate in the Miglyol® 812 under continuous stirring and maintain this until the aluminium distearate is dissolved completely.
3. Let the mixture cool down to 60° C. under homogenisation
4. Add the cefquinome sulphate under homogenisation
5. Let the mixture cool down to 25° C. under homogenisation The pharmaceutical compositions provided by this invention have been evaluated in several tests designed to show the utility and efficacy.
The following in vivo pharmacokinetic experiments in cattle, pigs and dogs show the prolonged release profile of the tested formulations in the target species.

Example 2

One such test consisted of treating cattle (bw 270–350 kg) with cefquinome sulphate in the prolonged release formulation containing varying amounts of cefquinome sulphate after sc application of 5 mg/kg bw. The tested prolonged release formulation contained a) 7.5% (w/v) cefquinome sulphate, 3% aluminium distearate ad 100 Miglyol® 812, b) 10% (w/v) cefquinome sulphate, 3% aluminium distearate ad 100 Miglyol® 812, c and d) 15% (w/v) cefquinome sulphate, 3% aluminium distearate ad 100 Miglyole 812. The formulations were administered at a single dose subcutaneous into the neck. Blood samples were collected by jugular venipuncture at times 0, 1, 2, 4, 6, 8, 10, 12, 24, 28, 30, 32, 48, 52, 56 and 72 h after drug administration.

Concentrations of cefquinome in each plasma sample were determined by a microbiological technique (bioassay to quantify cefquinome in biological fluids) with *Streptococcus* (Str.) pyogenes A 77 as test organism. The Str. pyogenes A77 suspension and sheep erythrocytes were added to Mueller-Hinton agar and after mixing allowed to cool to form a layer of about 2 mm thickness. Aliquots of standard samples (sample concentrations that were intended to bracket the range of concentrations expected in experimental plasma samples) and experimental samples were pipetted into agar wells of 13 mm diameter. Prediffusion time was one hour before incubating at 35° C. for 18 hours. Areas of bacterial growth showed hemolysis, the diameters of zones without hemolysis were taken as the measure of the amount of antibiotic present. The lowest standard sample concentration at which a zone of inhibition was detectable was taken as limit of quantitation.

The limit of quantitation (LOQ) of this assay is 10 ng/mL plasma. This method was used in all following experiments for determination of cefquinome.

Figure 1:
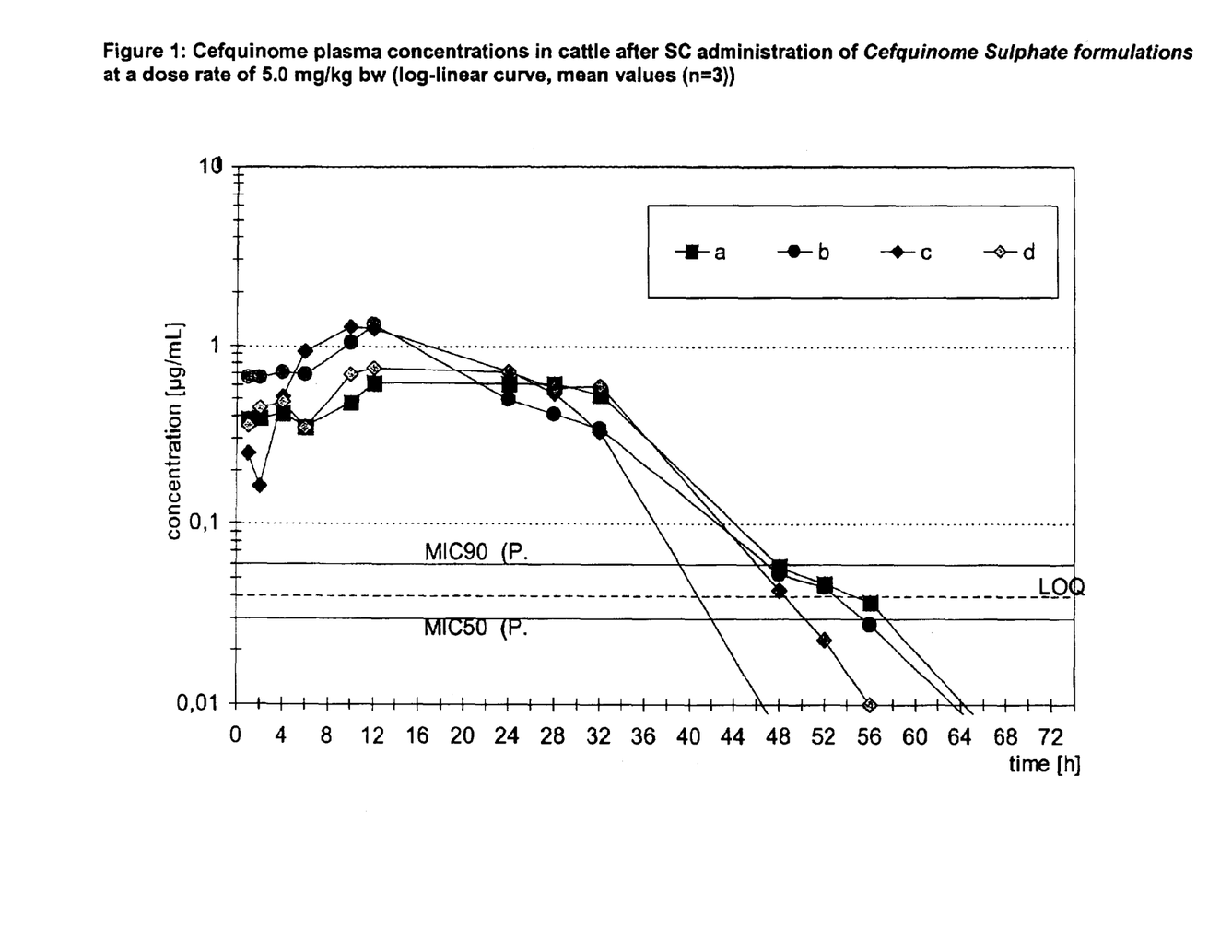
FIG. 1 shows bovine plasma cefquinome concentrations (μg/mL after single sc administration of cefquinome sulfate composition at a concentration of 7.5%, 10% and 15%.

FIG. 1 shows bovine plasma cefquinome concentrations ($\mu$g/mL) after single sc administration of cefquinome sulfate composition at a concentration of 7.5%, 10% and 15%. The results obtained show that plasma concentrations above MIC 90 can be maintained over a period of more than 32 hours and therefore a suitable prolonged release profile was reached. There were no technological problems (syringeability, re-suspendability, residues in animal) detectable.

Example 3

The pharmacokinetic profile of the prolonged release cefquinome sulphate formulation according to the invention in dogs (10–20 kg bw) after sc application of 5 mg/kg bw and 10 mg/kg bw was assessed in this study. The tested prolonged release formulation contained 7.5% (w/v) cefquinome sulphate, 3% aluminium distearate ad 100 Miglyol® 812. The formulation was administered at a single dose subcutaneous into the neck. Blood samples were collected by jugular venipuncture at times 0, 0.5, 1, 2, 3, 4, 6, 8, 10, 24, 26, 28, 30, 32, 48, 56 and 72 h after drug administration. The concentration of cefquinome in plasma sample was determined by bioassay.

Figure 2:
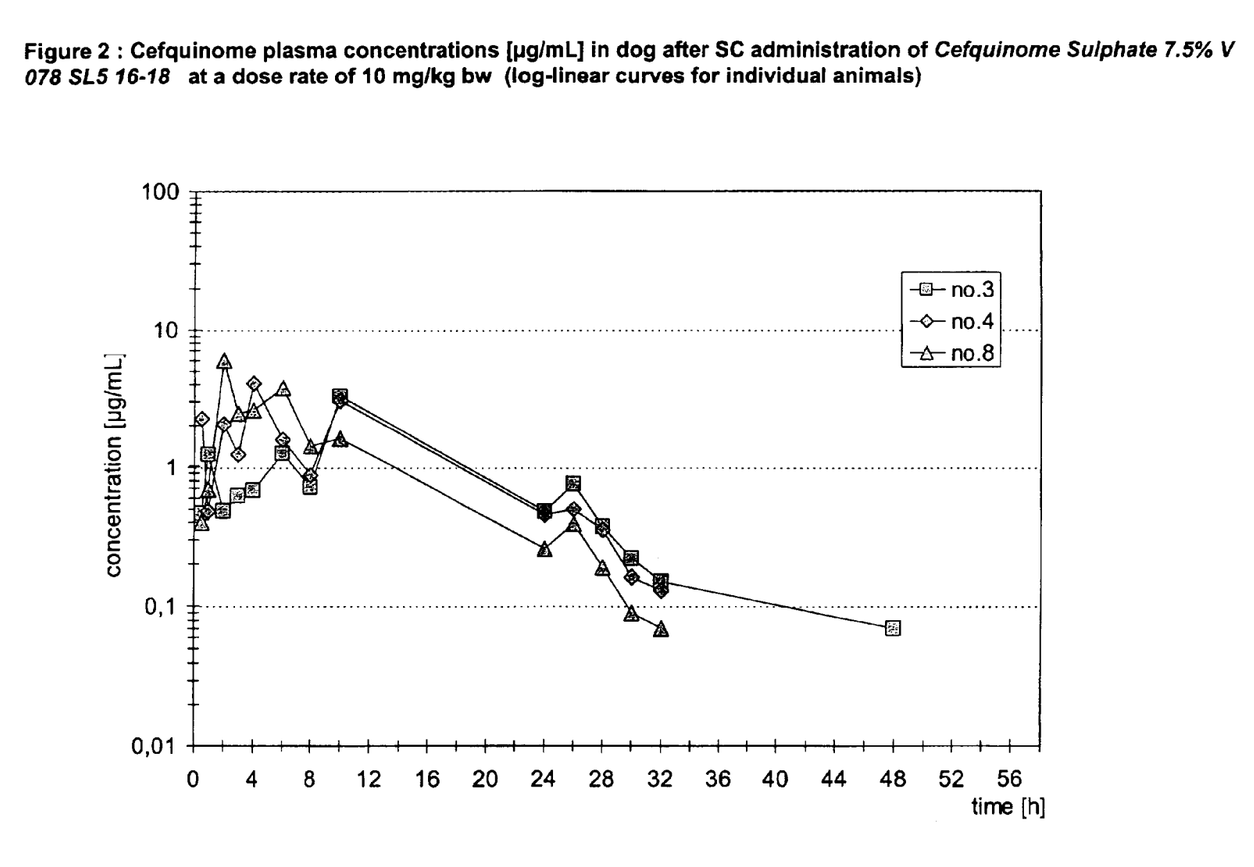
FIG. 2 shows plasma cefquinome concentrations (individual animals in μg/mL) after single sc administration of the formulations to dogs.

FIG. 2 show plasma cefquinome concentrations (individual animals in $\mu$g/mL) after single sc administration of the formulations to dogs. The results obtained show that in dogs effective plasma concentrations can be maintained over a period of more than 32 hours and therefore a suitable prolonged release profile was reached.

Example 4

The pharmacokinetic profile of the prolonged release cefquinome sulphate formulation according to the invention in pigs (30–50 kg bw) after sc application of 10 mg/kg bw was assessed in this study. The tested prolonged release formulation contained 7.5% (w/v) cefquinome sulphate, 3% aluminium distearate ad 100 Miglyol® 812. The formulation was administered at a single dose subcutaneously into the neck. Blood samples were collected by jugular venipuncture at times 0, 0.5, 1, 2, 3, 4, 6, 8, 10, 24, 26, 28, 30, 32, 48, 56 and 72 h after drug administration. The concentration of cefquinome in plasma sample was determined by bioassay.

Figure 3:
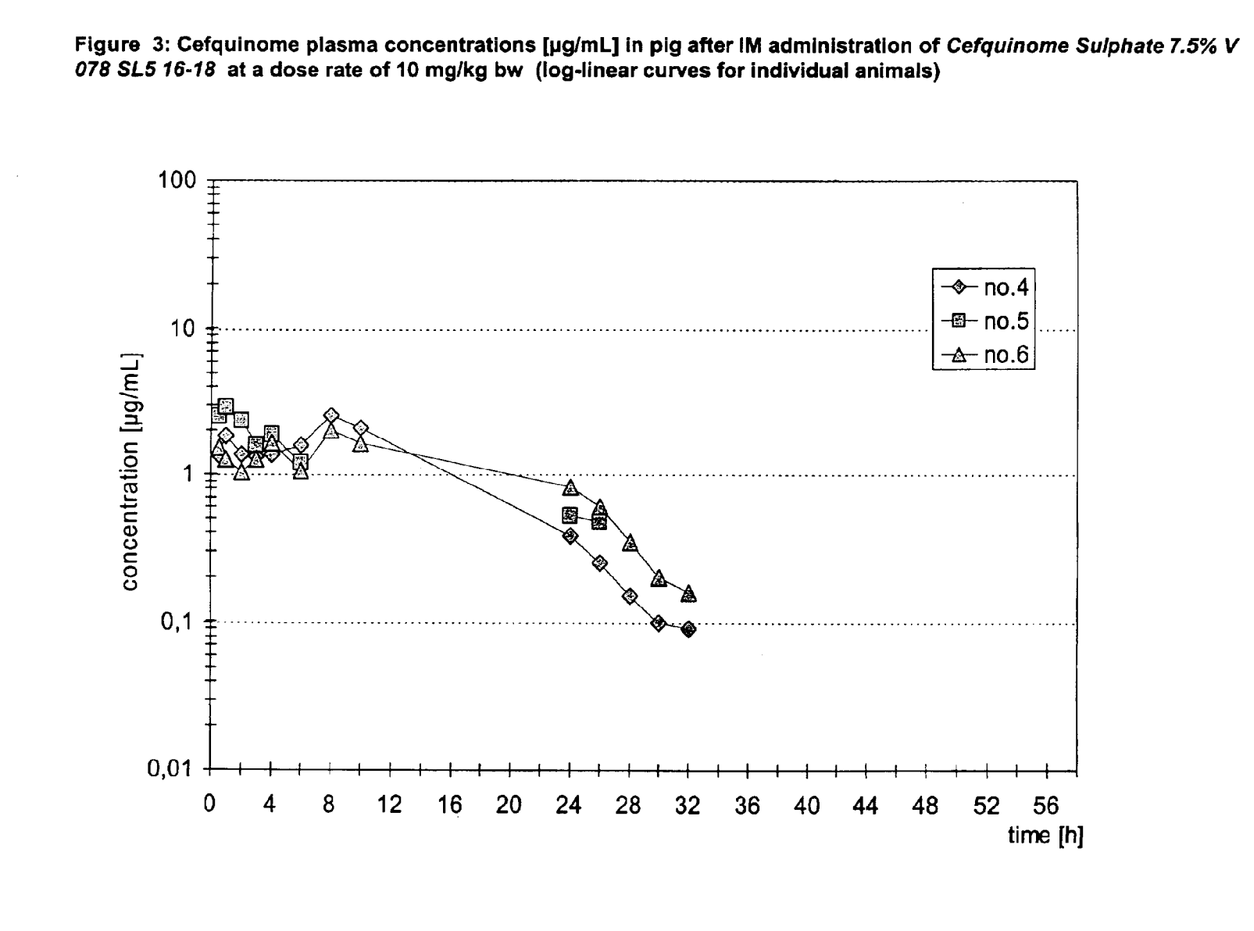
FIG. 3 shows plasma cefquinome concentrations (individual animals in μg/mL) after single sc administration of the formulation to pigs.

FIG. 3 shows plasma cefquinome concentrations (individual animals in $\mu$g/mL) after single sc administration of the formulation to pigs. The results obtained show that in pigs effective plasma concentrations can be maintained over a period of more than 24 hours and therefore a suitable prolonged release profile was reached.

Example 5

The pharmacokinetic profiles of two different cefquinome sulphate formulations with cellulose based slow release excipients were compared in this study, each formulation in three different dosages (1, 3 and 5 mg/kg bodyweight) in a group of 3 cattle per dose (bodyweight 200–400 kg). Formulations tested: Lot No. 96906/96907 cefquinome sulphate, span, ethylcellulose, hydroxypropylmethylcellulose (HPMC) 1 (96906) and 2 (96907), Miglyol® 812.

The formulations were administered at a single dose subcutaneous (sc) into the neck. Each animal received each of the preparations once with a 7 days washout period between the administrations (cross over design).

Blood samples were collected by jugular venipuncture at times 0, 1, 2, 4, 6, 8, 24, 32, 48, 56, and 72 h after drug administration.

Figure 4:
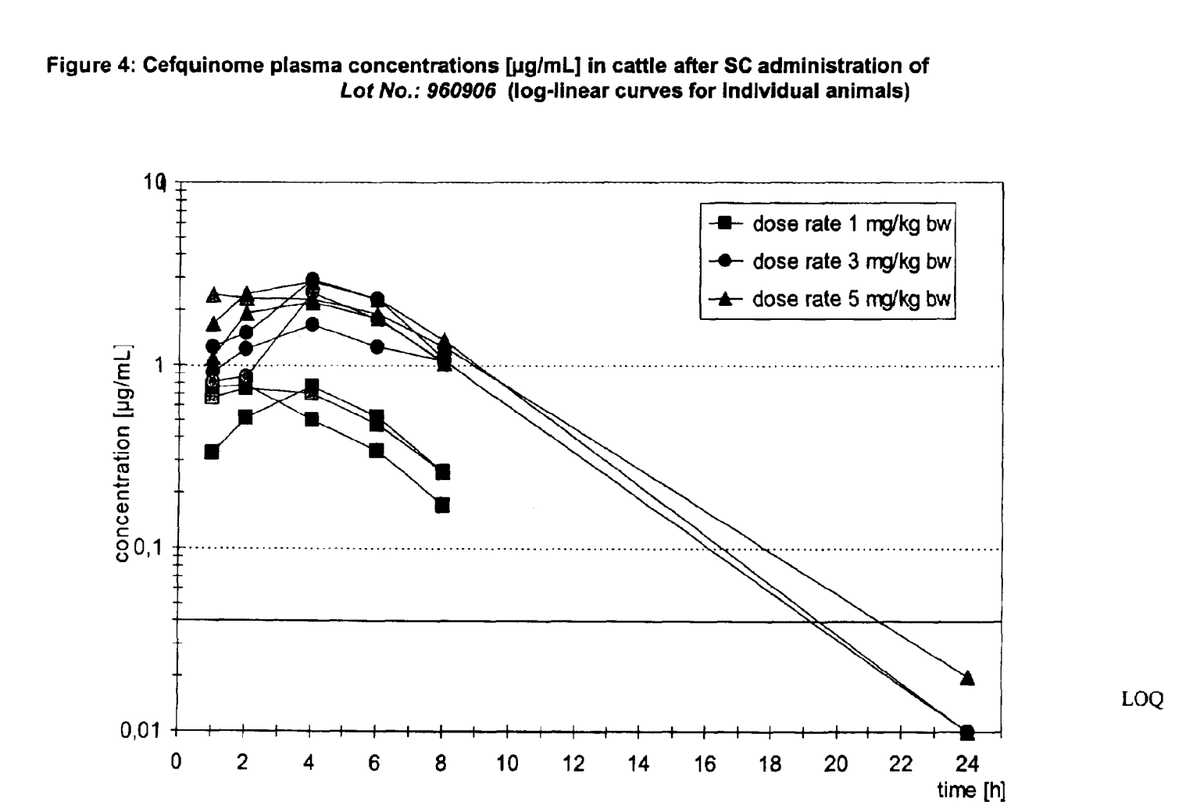
FIGS. 4 and 5 show bovine plasma cefquinome concentrations (individual animals) after sc administration of Lot No. 96906 and Lot 96907.
Figure 5:
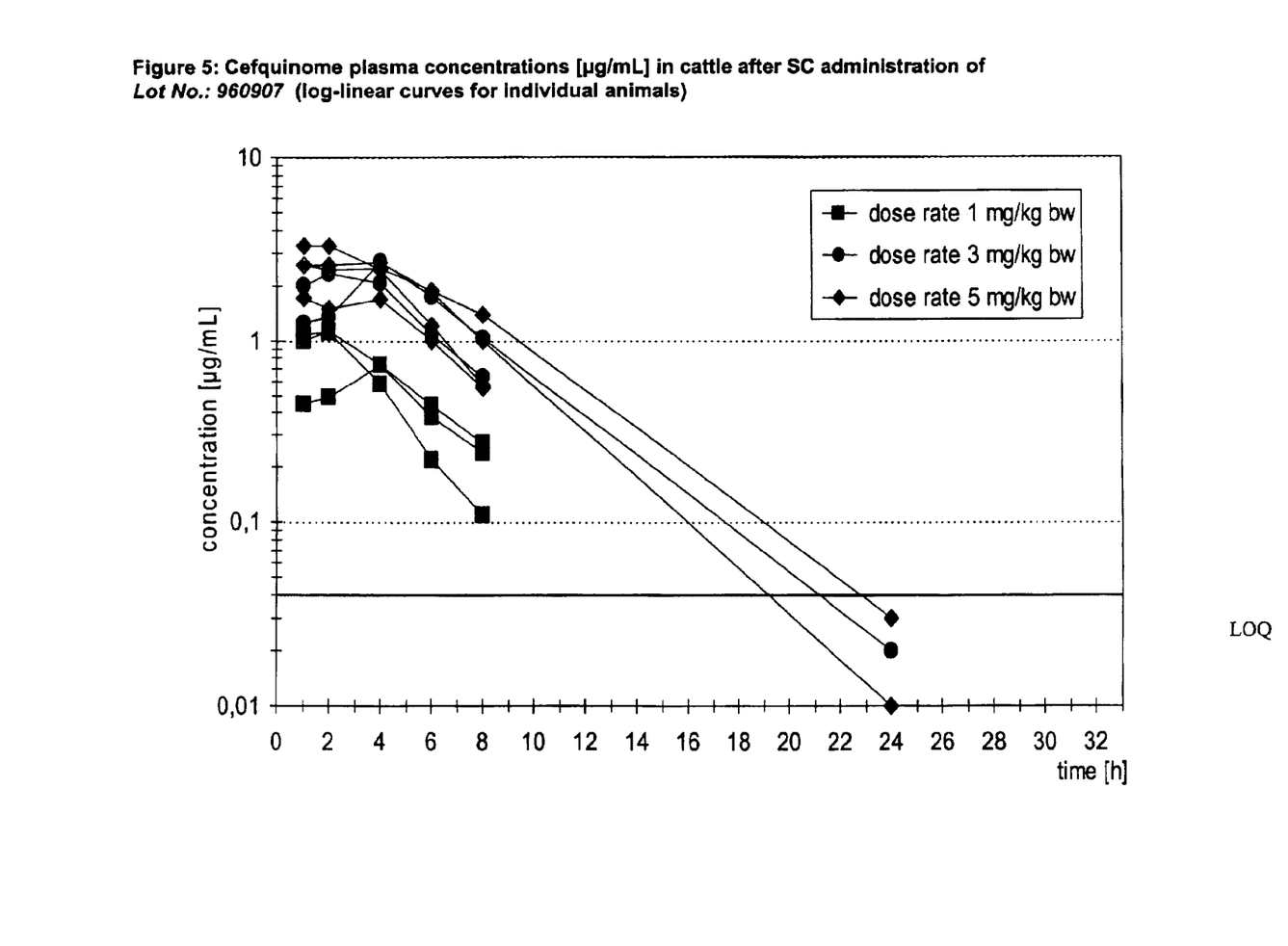

FIGS. 4 and 5 show bovine plasma cefquinome concentrations (individual animals) after sc administration of Lot No. 96906 and Lot 96907. The results obtained show that the two tested formulations can not maintain therapeutic blood levels for more than 24 hours and therefore do not provide a suitable in vivo pharmakokinetic prolonged release profile.

In a further experiment a pharmaceutically preparation on more different cellulose slow release excipients as described in FR 2685203 was evaluated and the results obtained show that the tested formulations can not maintain therapeutic blood levels for more than 24 hours.

Example 6

The pharmacokinetic profile of five different cefquinome sulphate formulations was assessed in this study by a parallel comparison with cefquinome sulphate in ethyloleate oily suspension. Each formulation was administered in a dose of 5 mg/kg bw in a group of 3 animals per group (bw 150–210 kg). Lot 970802, 970804 and 97903 contained cefquinome sulphate and cellulose based excipients. Lot 970803 contained cefquinome naphthoate and cellulose based excipients. Lot 970805 contained cefquinome sulphate and aluminium-monostearate (AMS) based excipients. The formulations were administered at a single dose subcutaneous (sc) into the neck. Blood samples were collected by jugular venipuncture at times 0, 0.5, 1, 2, 3, 4, 6, 8, 10, 24, 32, 48, 56 and 72 h after drug administration. Concentrations of cefquinome in each plasma sample were determined by bioassay.

Figure 6:
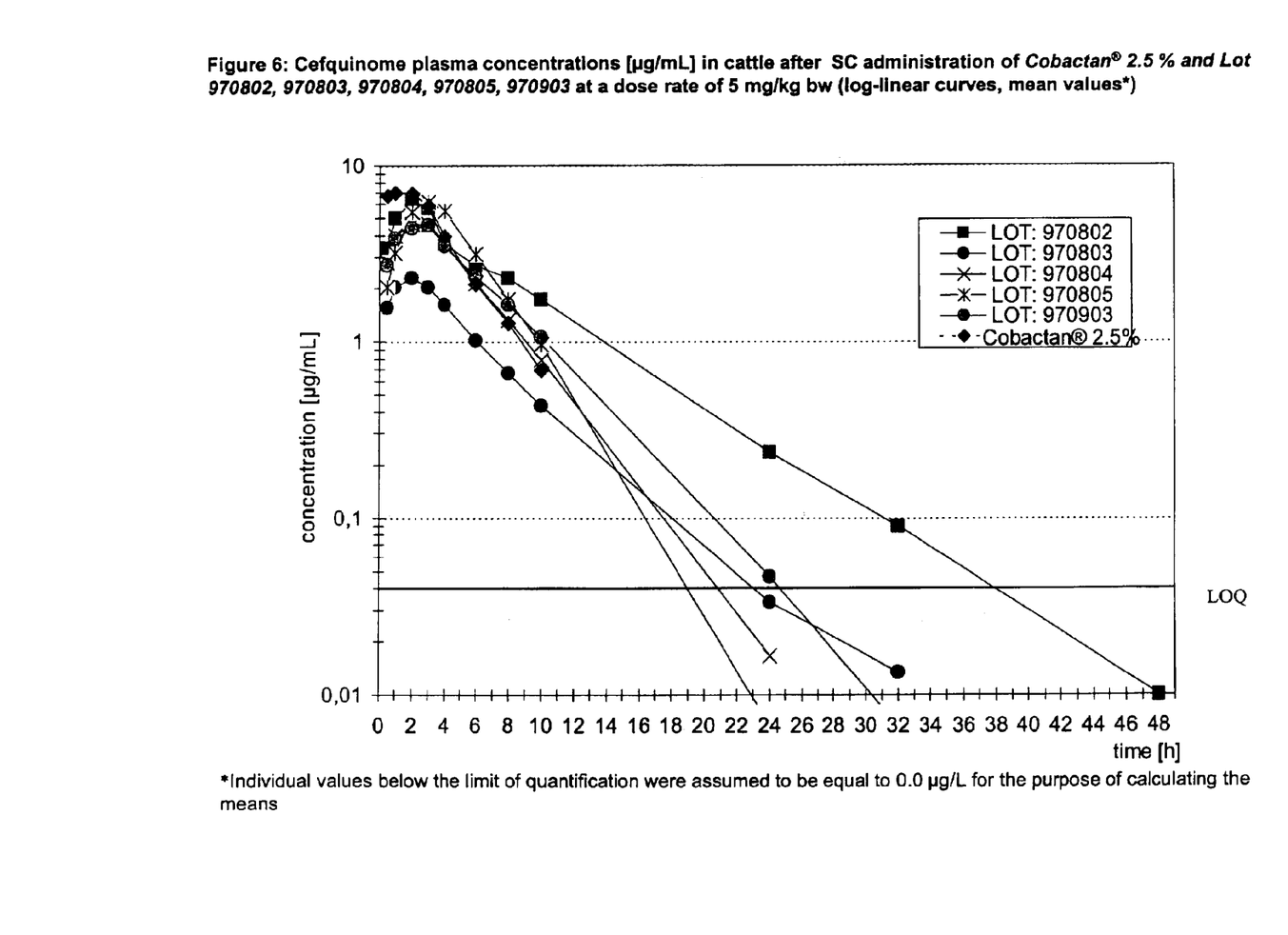
FIG. 6 shows bovine plasma cefquinome concentrations (mean values in μg/mL) after cc administration of the formulations at a dose rate of 5 mg/kg bw.

FIG. 6 shows bovine plasma cefquinome concentrations (mean values in $\mu$g/mL) after sc administration of the formulations at a dose rate of 5 mg/kg bw. The results obtained show that the tested formulations 970803, 970903, 970804, 970805 can not maintain therapeutic blood levels for more than 32 hours. The formulation 970802 (cellulose based) provided a suitable prolonged release profile, but due to technological problems (re-suspendability was impossible) an industrial development was not considered.

Example 7

The pharmacokinetic profile of prolonged release cefquinome formulation in cattle (bodyweight 145–400 kg) after microencapsulation of the active ingredient (microspheres) in a matrix of partially hydrogenated vegetable fat in a dosage of 5 mg/kg bw was assessed in this study by a parallel comparison with the reference preparation. The tested prolonged release formulations contained: a–d) Cefquinome sulphate suspended in ethyloleate (reference preparation), e) Cefquinome sulphate microspheres suspended in an aqueous carrier solution.

The formulations were administered at a single dose subcutaneous (sc) into the neck. Each animal received each of the preparations once with a 7 days washout period between the administrations.

Blood samples were collected by jugular venipuncture at times 0, 0.5, 1, 1.5, 2, 3, 4, 6, 8, 24, 32, 48, 56 and 72 h after drug administration. The concentration of cefquinome in plasma samples was determined by bioassay.

Figure 7:
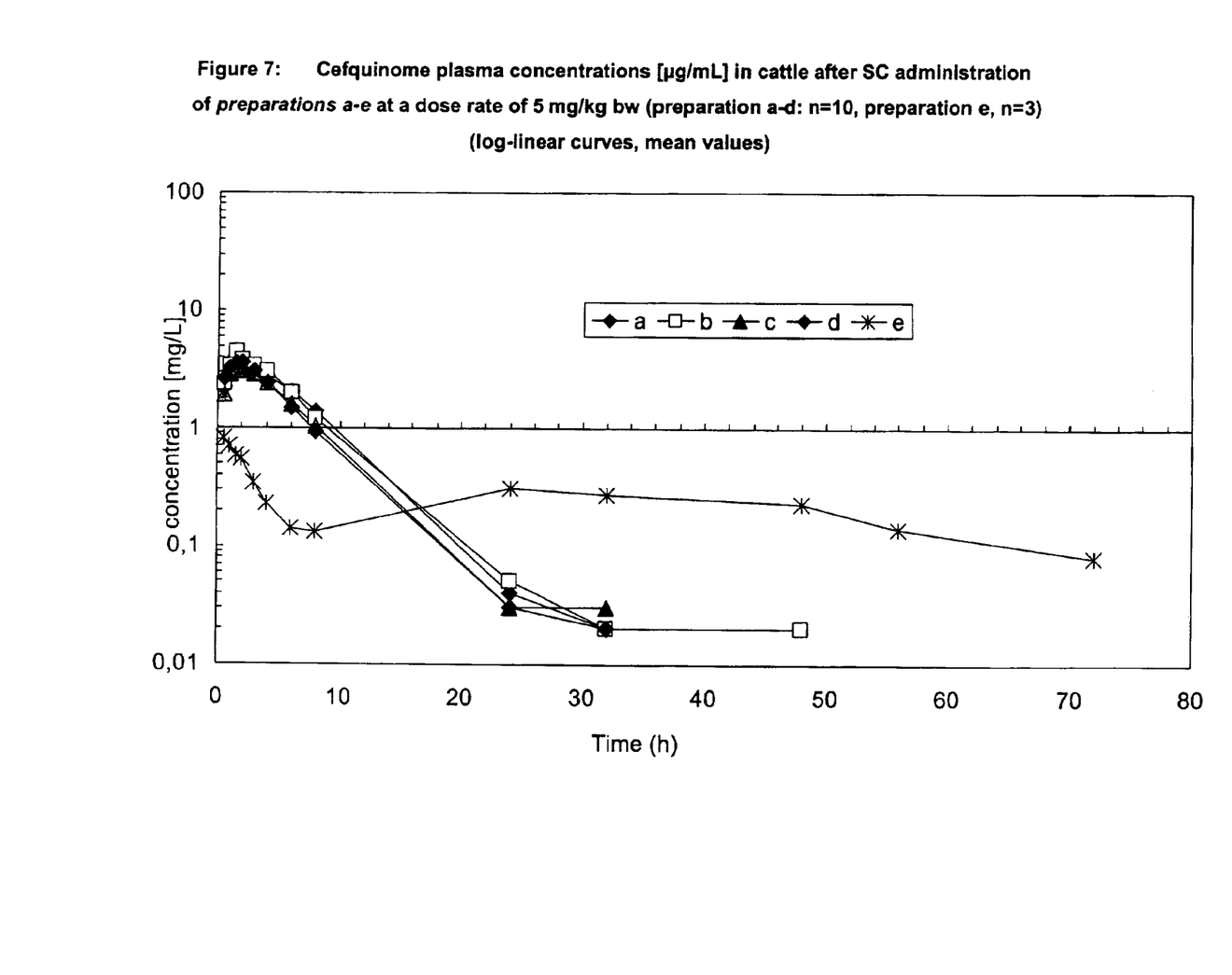
FIG. 7 shows bovine plasma cefquinome concentrations (mean values in μg/L) after sc administration of the formulations.

FIG. 7 shows bovine plasma cefquinome concentrations (mean values in mg/L) after sc administration of the formulations. The microsphere formulation (No. e) provides a prolonged release profile of the active ingredient. The microspheres in the used form were however very poorly re-suspendable arid sedimentation took place very soon, even in the syringe. Therefore the development of an industrial application of this type of formulation was not followed up.

Example 8

The pharmacokinetic profile of different prolonged release cefquinome formulations at a dosage of 5 mg/kg bw was assessed in this study by a parallel comparison with the reference preparation in cattle (bw 200–400 kg).

The tested formulation contained:
0) Cobactan 2.5%—Cefquinome sulphate suspended in ethyl oleate (reference preparation)
a) Z2/78 Cefquinome sulphate (237.1 mg) suspended in ethyloleate+hydroxymethylcellulose (50 mg)
b) Z2/79 Cefquinome sulphate (237.1 mg) suspended in ethyloleate+starch glycolate sodium (300 mg)
c) Z2/80 Cefquinome naphthoate (271.2 mg) suspended in ethyloleate+hydroxymethylcellulose high viscosity (50 mg)
d) Z2/81 Cefquinome naphthoate (271.2 mg) suspended in ethyloleate+starch glycolate sodium (300 mg)

The formulations were administered at a single dose subcutaneous (sc) into the neck. Each animal received the preparations once with a 7 days washout period between the administrations.

Blood samples were collected by jugular venipuncture at times 0, 0.5, 1, 1.5, 2, 4, 6, 8, 24, 32, 48, 56, 72 and 80 h after drug administration. The concentration of cefquinome in plasma samples was determined by bioassay.

Figure 8:
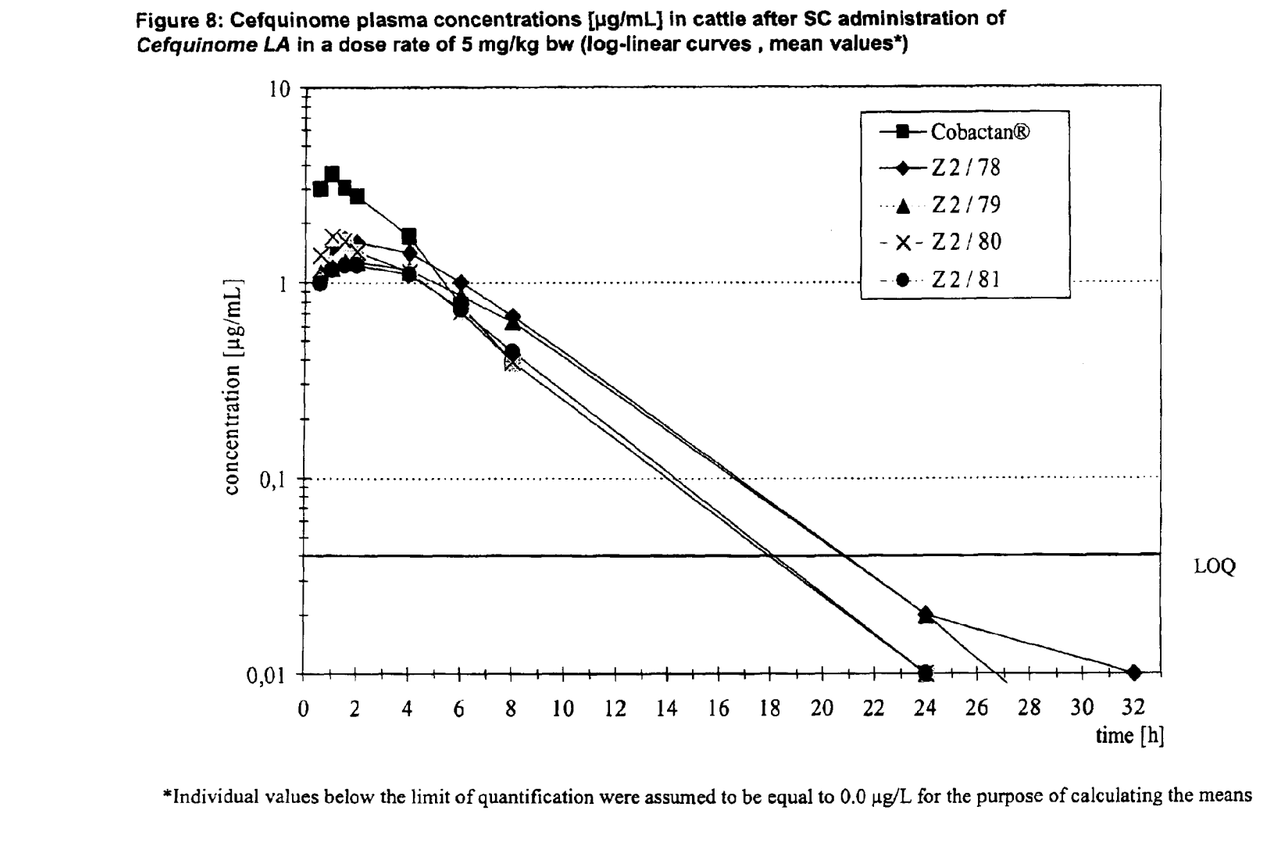
FIG. 8 shows bovine plasma cefquinome concentrations (mean values in μg/mL) after sc administration of the formulations.

FIG. 8 shows bovine plasma cefquinome concentrations (mean values in $\mu$g/mL) after sc administration of the formulations. The results obtained show that the tested formulations can not maintain therapeutic blood levels for more than 24 hours.

Example 9

The pharmacokinetic profile of a cefquinome sulphate formulation in a dosage of 5 mg/kg bw was assessed in this study by a parallel comparison with cefquinome ethyloleate oily suspension in a group of 3 cattle (bw 340–380 kg). The tested formulation contained cefquinome sulphate-p hydroxybenzoate and Miglyol® 812.

The formulations were administered at a single dose intramuscular (im) into the M. triceps brachii.

Blood samples were collected by jugular venipuncture at times 0, 0.5, 1, 2, 4, 6, 8, 10, 12, 24, 26, 28, 30, 32, 48, 56 and 72 h after drug administration. The concentration of cefquinome in plasma samples was determined by bioassay.

Figure 9:
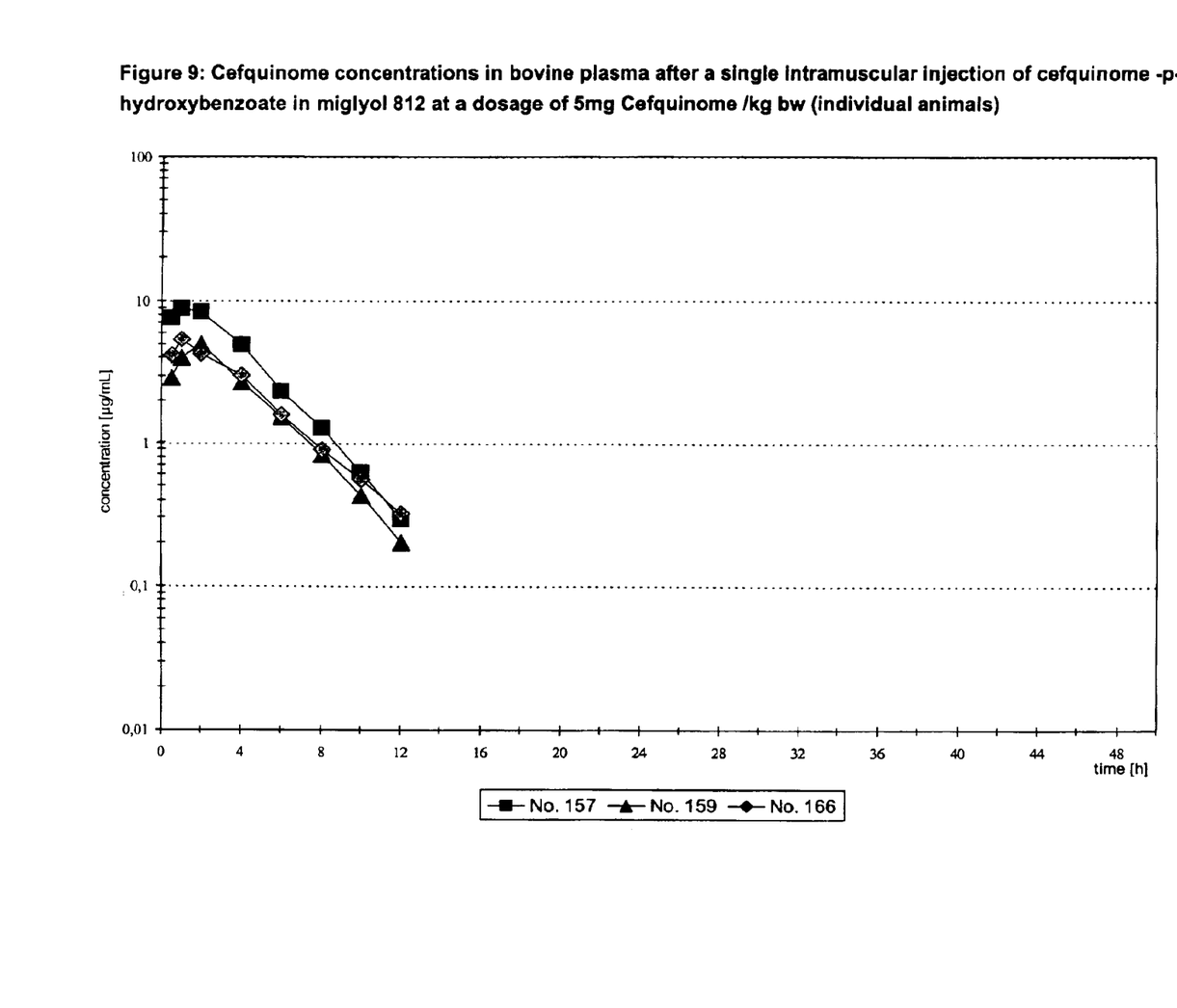
FIG. 9 shows bovine plasma cefquinome concentrations (individual animals in μg/mL) after single im administration of the formulation.

FIG. 9 shows bovine plasma cefquinome concentrations (individual animals in $\mu$g/mL) after single im administration of the formulation. The results obtained show that the tested prolonged release formulation maintained therapeutic blood levels only for 12 hours.

Example 10

The pharmacokinetic profile of prolonged release cefquinome formulations, that use various SABER® oil Delivery systems, in cattle (bodyweight 230–345 kg) and pigs (41 to 55 kg) in a dosage of 3 mg or 5 mg/kg bw im and sc to cattle and im 6 and 10 mg/kg bw im to pigs was assessed. The SABER Delivery system uses a high viscosity base compound (sucrose acetate isobutyrate, SAIB) to provide controlled release. Upon addition of a small amount of solvent (Ethanol (EtOH), Ethyl lactate (EtLac), the high viscosity component, SAIB converts to an easily injectable liquid. Once inside the body, the solvent dissipates and a semi-solid, biodegradable implant is formed. The tested prolonged release formulation are Lot 96557, Lot 96558, Lot 96559.

The formulations were administered at a single dose subcutaneous (sc) into the neck or intramuscular (im) in M. triceps brachii. Each animal received each of the preparations once with a 7 days washout period between the administrations.

Blood samples were collected by jugular venipuncture (cattle) and by puncture of the anterior Vena cava (pigs) at times 0, 1, 4, 6, 8, 24, 32, 48, 56 and 72 h after drug administration. The concentration of cefquinome in plasma samples was determined by bioassay. On validation of the method a limit of quantification (LOQ) of 0.04 µg cefquinome/mL plasma was established.

Figure 10:
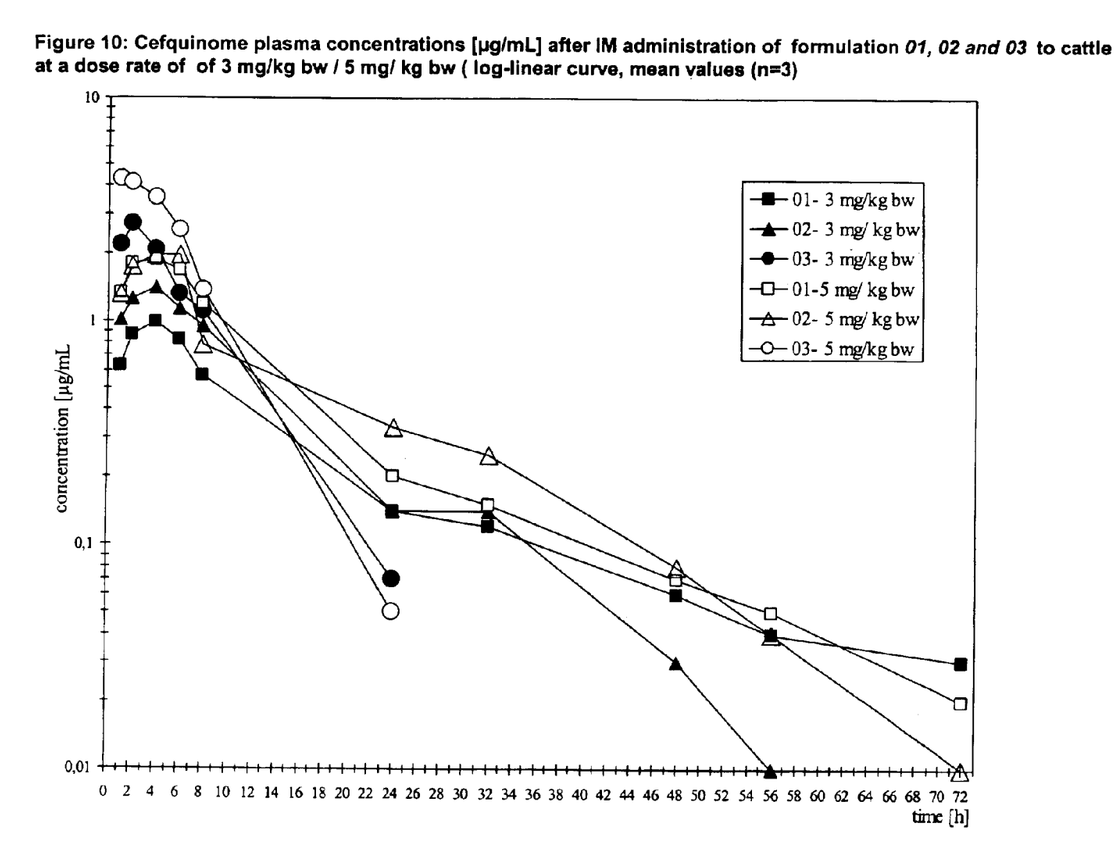
FIG. 10 shows bovine plasma cefquinome concentrations (μg/mL) after im administration of the formulations to cattle.
Figure 11:
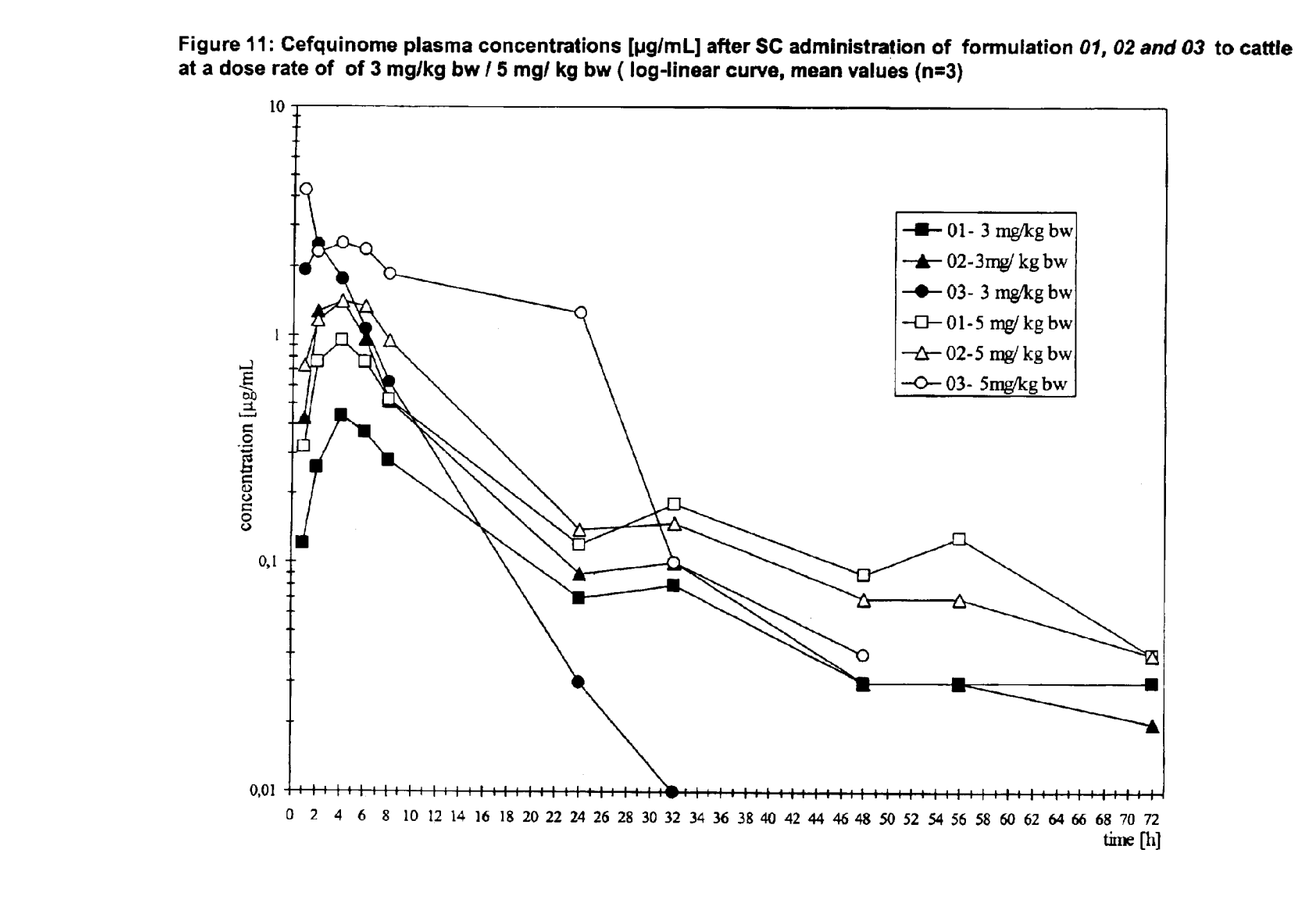
FIG. 11 shows bovine plasma cefquinome concentrations (μg/mL) after sc administration of the formulations to cattle.
Figure 12:
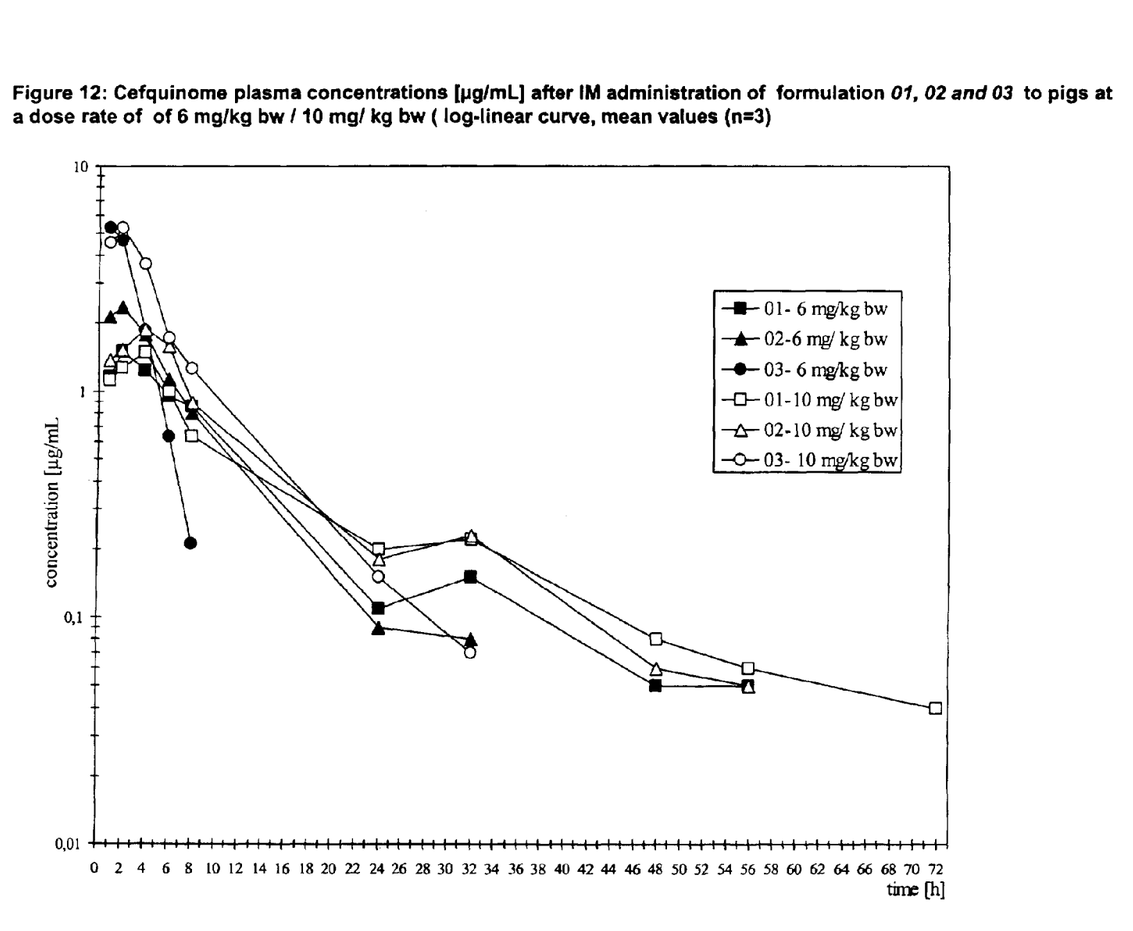
FIG. 12 shows porcine plasma cefquinome concentrations (μg/mL) after im administration of the formulations to pigs.

FIG. 10 shows bovine plasma cefquinome concentrations (µg/mL) after im administration of the formulations to cattle. FIG. 11 shows bovine plasma cefquinome concentrations (µg/mL) after sc administration of the formulations to cattle. FIG. 12 shows porcine plasma cefquinome concentrations (µg/mL) after im administration of the formulations to pigs.

The formulations a and b provided prolonged release pharmacokinetic profiles on a low level after sc, im administration to cattle and im administration to pigs, but the industrial development was not considered because of residues of the carrier in the animal body at the injection site, that were still detectable 6 months after the administration. The formulation c did not result in prolonged release profiles with activity >32 h in all applications to pigs and cattle.

What is claimed is:

1. An injectable pharmaceutical composition comprising a cefquinome and a prolonged release vehicle, wherein the prolonged release vehicle comprises a mixture of an oil and aluminium distearate.

2. A composition according to claim 1 comprising the aluminium distearate in an amount of 1.0 to 4.0% by weight.

3. A composition according to claim 2 comprising the aluminium distearate in an amount of 2.5 to 3.5% by weight.

4. A composition according to claim 1, wherein the oil is a medium chain triglyceride or a mixture of medium chain triglycerides.

5. A composition according to claim 4, wherein the oil is a polyethylene glycol di-ester of saturated fatty acids having a chain length of 8 to 10 carbon atoms.

6. A composition according to claim 1 comprising 2.0 to 20.0% by weight of a cefquinome.

7. A composition according to claim 6 comprising 7.5 to 10.0% by weight of a cefquinome.

8. A composition according to claim 7, wherein the cefquinome is cefquinome sulphate.

9. A process for preparing a pharmaceutical composition as defined in claim 1, comprising the steps of mixing the oil and the aluminium distearate to create the prolonged release vehicle and suspending the cefquinome in the prolonged release vehicle.

10. A process according to claim 9, wherein the aluminium distearate is added to the oil under gentle stirring and heating to form the prolonged release vehicle and the mixture is allowed to cool before adding the cefquinome.

11. A method for treating or preventing an infectious disease in an animal comprising administering an effective amount of a cefquinome in a single dose in a prolonged release vehicle comprising a mixture of an oil and aluminium distearate.

12. A method for treating or preventing a gram positive or grain negative bacterial infection comprising administering an effective amount of a cefquinome in a prolonged release vehicle comprising a mixture of an oil and aluminium distearate.

* * * * *